US00PP27032P2

(12) United States Plant Patent
Clark et al.

(10) Patent No.: US PP27,032 P2
(45) Date of Patent: Aug. 9, 2016

(54) BLACKBERRY PLANT NAMED 'APF-236T'

(50) Latin Name: *Rubus subgenus Rubus Watson.*
Varietal Denomination: APF-236T

(71) Applicant: Fall Creek Farm & Nursery, Inc., Lowell, OR (US)

(72) Inventors: John Reuben Clark, Fayetteville, AZ (US); Peter Stefan Boches, Eugene, OR (US)

(73) Assignee: Middle Fork Selections, LLC, Lowell, OR (US)

( * ) Notice: Subject to any disclaimer, the term of this patent is extended or adjusted under 35 U.S.C. 154(b) by 47 days.

(21) Appl. No.: 14/544,545

(22) Filed: Jan. 20, 2015

(51) Int. Cl.
*A01H 5/08* (2006.01)

(52) U.S. Cl.
USPC ..... Plt./203

(58) Field of Classification Search
USPC ..... Plt./203
CPC ..... A01H 5/0887
See application file for complete search history.

*Primary Examiner* — Kent L Bell
(74) *Attorney, Agent, or Firm* — Hahn Loeser & Parks, LLP

(57) ABSTRACT

A new and distinct cultivar of blackberry named 'APF-236T', characterized by its thornless canes, very dwarf growth habit, medium-large fruit, good fruit quality, and excellent primocane flower bud formation.

5 Drawing Sheets

Variety denomination: The new blackberry plant claimed is of the variety denominated 'APF-236T'.

BACKGROUND OF THE INVENTION

The new dwarf, thornless, primocane-fruiting cultivar of blackberry called 'APF-236T' is described herein. The new cultivar originated from a hand-pollinated cross of Arkansas selection A-120T (unpatented selection)×APF-132T (unpatented selection) made in 2007. The seeds resulting from this controlled hybridization were germinated in a greenhouse in the spring of 2008 and planted in a field near Clarksville, Ark. (West-Central Arkansas). The seedlings fruited in the summer of 2009, and one seedling, designated APF-236T, was selected for its thornless canes, very dwarf growth habit, medium-large fruit, good fruit quality, and excellent primocane flower bud formation.

SUMMARY OF THE INVENTION

The new and distinct cultivar of blackberry originated from a hand-pollinated cross of Ark. Selection APF-120T (non-patented, unreleased genotype)×APF-132T (non-patented, unreleased genotype) made in 2007 and located near Clarksville, Ark. (West-Central Arkansas). The botanical designation of the new cultivar of blackberry is *Rubus* subgenus *Rubus* Watson. The seeds resulting from this controlled hybridization were germinated in a greenhouse in the winter to early spring of 2008 and planted in a field near Clarksville, Ark. The seedlings fruited in the summer of 2009 on floricanes and one seedling, designated APF-236T, was selected for its thornless canes, very dwarf growth habit, medium-large fruit, good fruit quality, and excellent primocane flower bud formation.

During 2009, the original plant selection was propagated asexually from root cuttings at the above-noted location, and a test row of 20 plants was established. Additionally, the cultivar has been tested at test plots in Lowell, Oreg., established in 2010 and at this location propagation was from root cuttings from the Clarksville, Ark. test plot plants.

The new cultivar has been asexually multiplied annually since 2009 by the use of root cuttings and by rooting adventitious shoots from root cuttings. It forms new shoots from adventitious buds on root cuttings readily. It has been asexually multiplied by the use of tissue culture in Lowell, Oreg., since 2012. During all asexual multiplication, the characteristics of the original plant have been maintained and no aberrant phenotypes have appeared.

Its primocane fruiting performance is substantially better in more moderate summer climates such as Lowell, Oreg., as evidenced by larger fruit weight and higher yields compared to Clarksville, Ark. The cultivar differs from most blackberry cultivars which are floricane fruiting. The cultivar has been observed in multiple plant plots since 2009 in Arkansas and since 2010 in Oregon and the plants canes have never grown taller than 1.5 m at either location. The combination of a thornless, primocane fruiting blackberry with dwarf stature is distinct from all other blackberry cultivars that are commercially available, to the best of our knowledge.

BRIEF DESCRIPTION OF THE DRAWINGS

The accompanying photographic illustration shows typical specimens in full color of the foliage and fruit of the new variety 'APF-236T'. The colors are as nearly true as is reasonably possible in a color representation of this type.

DETAILED BOTANICAL DESCRIPTION

Figure 1:
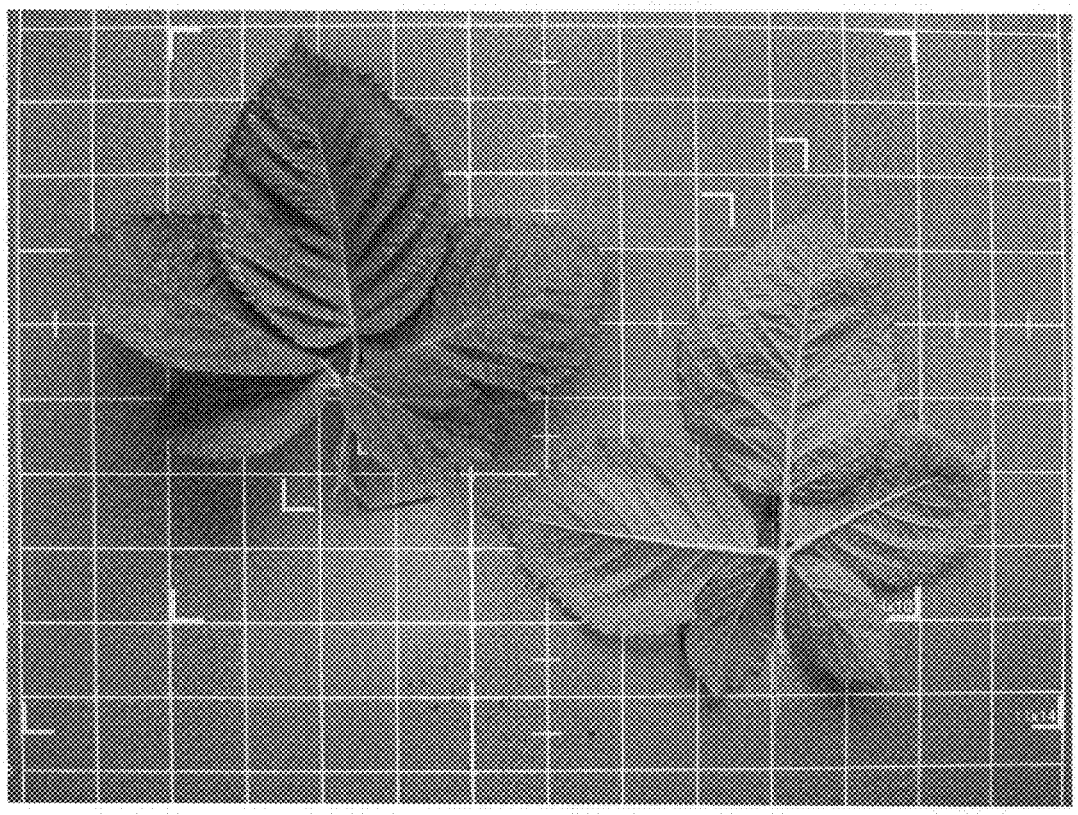
FIG. 1 is a photograph of the abaxial and adaxial side of a primocane leaf, taken in 2013, near Clarksville, Ark. of 'APF-236T'.
Figure 2:
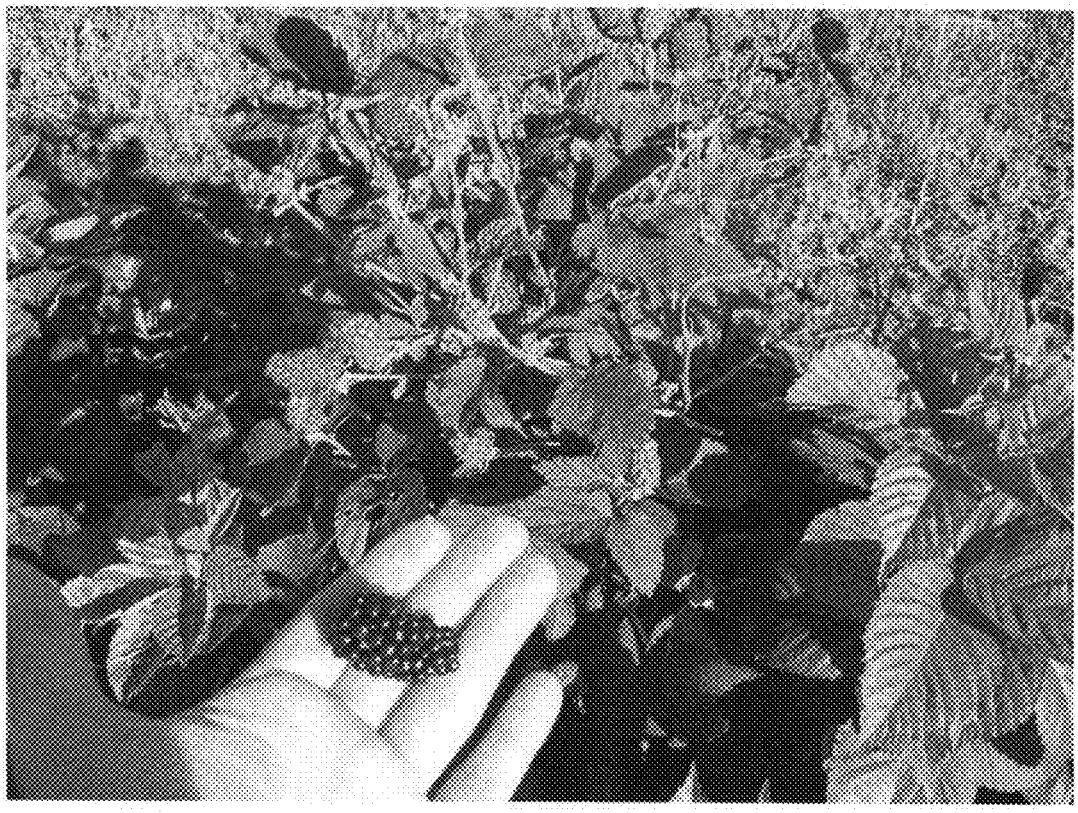
FIG. 2 is a photograph of an individual floricane fruit being held in front of a fruiting floricane, taken on Jun. 7, 2013, near Clarksville, Ark. of 'APF-236T'.
Figure 3:
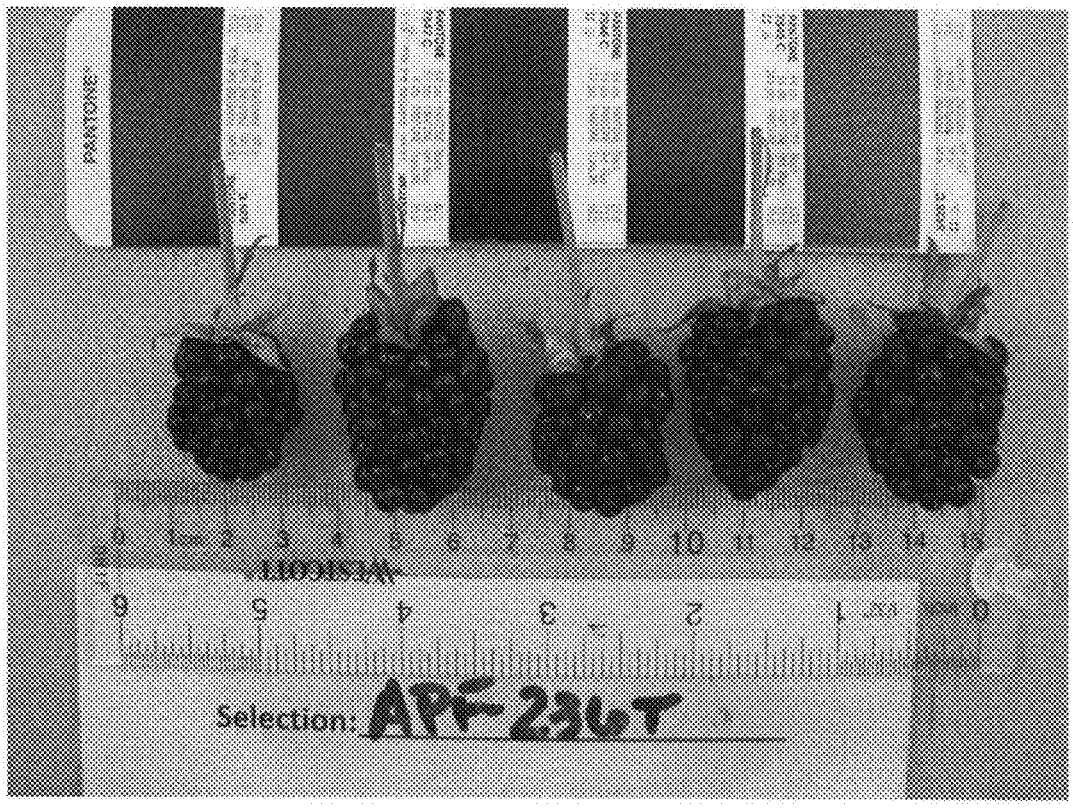
FIG. 3 is a photograph of primocane fruit placed next to a ruler and Pantone color references taken on Sep. 23, 2013 near Lowell, Oreg. of 'APF-236T'.
Figure 4:
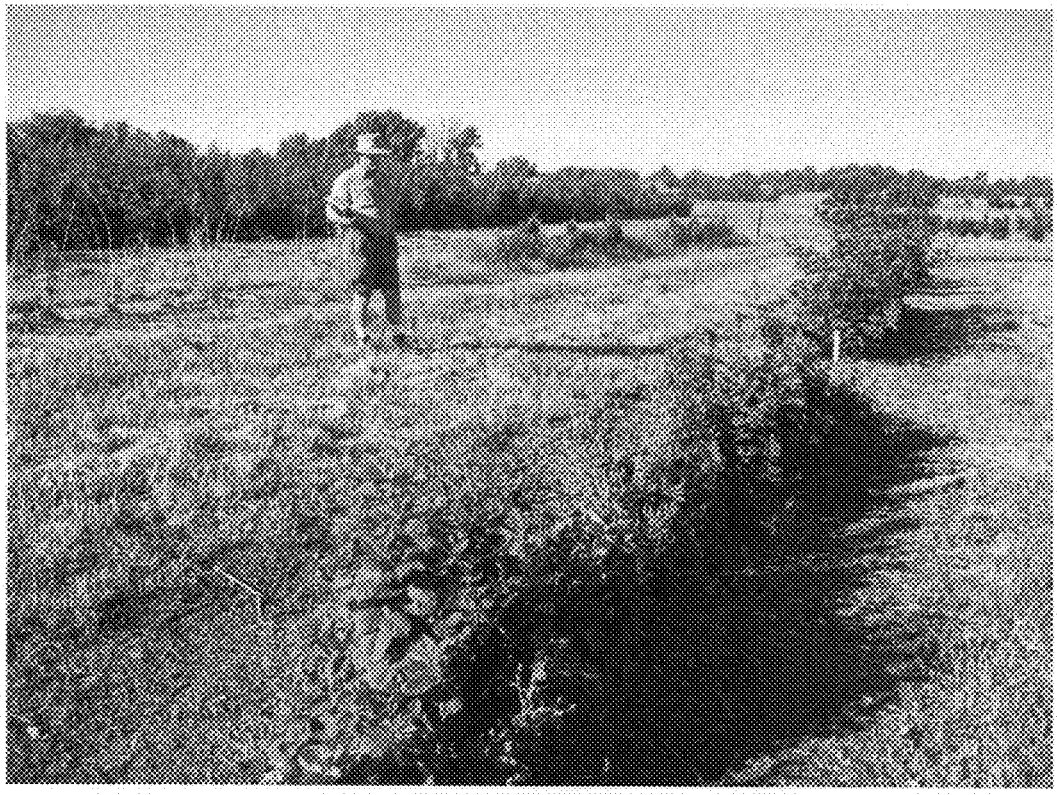
FIG. 4 is a photograph of four year old plants fruiting on floricanes, taken on Jun. 7, 2013 near Clarksville, Ark. of 'APF-236T'. Note the dwarf stature of 'APF-236T' (foreground) relative to typical erect blackberry plants behind Dr. John Clark.
Figure 5:
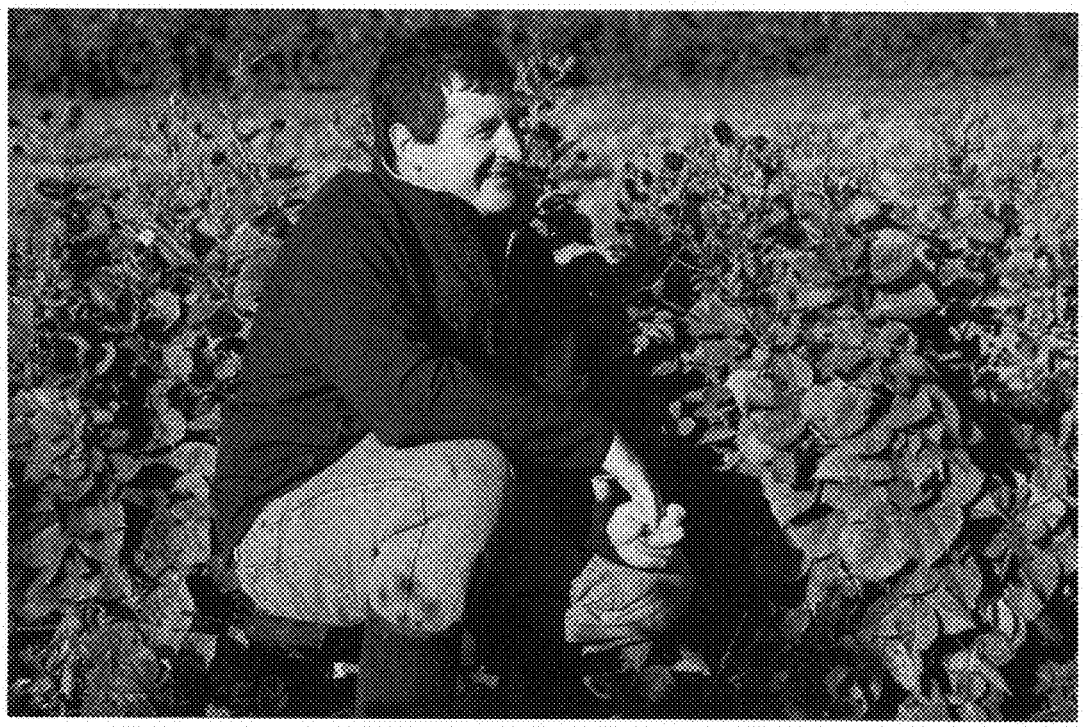
FIG. 5 is a photograph of two year old plants fruiting on primocanes, taken on Sep. 27, 2012 near Lowell, Oreg. of 'APF-236T'. Note the dwarf stature of 'APF-236T' relative to Dr. Peter Boches kneeling in the foreground.

The following detailed description sets forth the distinctive characteristics of 'APF-236T'. The data which defines these characteristics was collected from asexual reproductions of the original selection. 'APF-236T' has not been observed under all possible environmental conditions. Description is in accordance with UPOV terminology. Dimensions, sizes, colors, and other characteristics are approximations and averages set forth as accurately as possible. Color designations, color descriptions, and other phenotypical descriptions may deviate from the stated values and descriptions depending upon variation in environmental, seasonal, climatic and cultural conditions.

Plants and fruit of this new cultivar differ phenotypically from its parents. The new cultivar is thornless, ripens later on floricanes, has 1% lower soluble solids measurement, and lower productivity potential than parent APF-132, which is thorny. The new cultivar has larger fruit, better productivity potential and better flavor than parent APF-120. Both parents are of the dwarf, short internode architecture and are siblings. Although blackberries (*Rubus* subgenus *Rubus* Watson) are highly heterogeneous and outcrossing, and most clones contain genes from more than one species, the new cultivar and its progenitor lines phenotypically exhibit characters predominately of the erect eastern United States species, *Rubus allegheniensis* Porter (highbush blackberry).

Plants of the new cultivar are moderately vigorous with good row establishment following planting. Both primocanes and floricanes are erect in growth habit. The canes are self-supporting and do not require trellising during fruiting. The plants are thornless. The plants are moderately susceptible to downy mildew (caused by the pathogen *Peronospora sparsa* Berk.).

Unless noted otherwise, all botanical data pertaining to floricanes were collected near Clarksville, Ark. and all botanical data pertaining to primocanes were collected near Lowell, Oreg. The floricane bloom period of the new cultivar begins on 1 May, reaches its peak on 7 May, and finishes on 25 May. Primocane bloom period begins 12 July in Lowell, Oreg., reaches its peak on 26 July, and continues into October or the first hard freeze.

Floricane fruit of the new cultivar begins ripening 12 June. Primocane fruit was ripe beginning September 1st on tipped primocanes near Lowell, Oreg. The fruit is oblong to slightly ovate in shape and shiny black in color. The floricane fruit is medium (approximately 7 g). Primocane fruit in Lowell, Oreg. of the new cultivar averaged 6.4 g/berry.

The fresh fruit rates good in flavor. The flavor is sweet and mildly acidic, with low amounts of the bitterness that is present in some blackberries. The soluble solids concentration averages 10.4% on shiny black fruit harvested from floricanes. Floricane fruit and flower clusters are medium-large, cymose, and are mostly borne on the periphery of the plant canopy, providing easy access to harvest. Flower fertility is high and clusters are well filled.

Primocane fruit and flowers are borne on the cane terminus or on lateral branches if primocanes are tipped, and fruiting continues down the primocane during the season. Canes usually attain a length of 0.5 m prior to the appearance of flower buds. The number of nodes down the cane that develop flowers is largely dependent on the length and conditions of the late summer to fall growing period.

The following is a detailed description of the botanical and pomological characteristics of the subject blackberry. Color data are presented in Royal Horticultural Society Colour Chart designations (1986 2nd edition). Where dimensions, sizes, colors, and other characteristics are given, it is to be understood that such characteristics are approximations of averages set forth as accurately as practicable.

Plants used for botanical description of primocanes and parts of the primocanes (leaves, flowers, and fruit) were three years old and grown on a Camas sandy skeletal soil with drip irrigation near Fall Creek, Oreg. The plants used for primocane data collection were fertilized in April and again in June with a complete granular fertilizer at a rate of 14 to 40 g (0.5 to 1.5 oz) actual nitrogen per plant per year (depending on plant age). Primocanes were tipped at approximately 60 cm (24 inches).

Plants used for botanical description of floricanes and portions of the floricanes were three years old and grown on a fine sandy loam soil with sprinkler irrigation near Clarksville, Ark. The plants were fertilized near budbreak (late March on average) with complete or nitrogen fertilizer, and had an additional nitrogen fertilizer application in early July. Primocanes were not tipped and attained a total height of approximately 0.9 m (36 inches). Weeds were controlled with pre- and postemergence herbicides supplemented with mechanical weed control activities. A single application of liquid lime sulfur was applied to the plants at budbreak, but no other fungicides were used.

Plant:

*Size*.—Small. Plants are grown in a short hedgerow and primocanes tipped at approx., 60 cm; plants in this system range in size from approx. 75-150 cm tall and 75-102 cm wide.

*Growth habit*.—Moderate vigor, canes erect; suckers from crown and roots.

*Growth rate*.—First emergence of primocanes is 5 May and primocanes reach tipping height (50 cm) on 20 May.

*Productivity*.—Yield was not measured as this is a home garden/ornamental variety for which plant appearance and fruit quality are more important than yield. However, in general the new cultivar has good productivity.

*Cold hardiness*.—A low temperature of 5° F. near Clarksville, Ark. in the winter of 2014 resulted in the elimination of most of the crop on floricanes. Only a very few buds survived this temperature and cane damage was noted also.

Canes: Thornless, erect.

*Floricane* (*dormant or winter cane*).—Cane diameter: Base average 10.8 mm; midpoint average 8.7 mm; terminal average 4.7 mm. Internode length: Base average 40 mm; midpoint average 21.1 mm; terminal average 26.9 mm. Floricane color: Base Green Group (143C); midpoint Grayed-purple (183B); terminus Grayed-purple (183A).

*Primocane* (*current-season cane*).—Cane diameter: Base average 14.0 mm; midpoint average 13.4 mm; terminal average 2.5 mm. Internode length: Base average 27.1 mm; midpoint average 45.1 mm; terminal average 24.6 mm. Primocane color: Base Yellow-Green Group (144B); midpoint Yellow-Green Group (144B); terminus Yellow-Green Group (144B). Date of primocane emergence: 5 May.

Disease resistance: No particular disease susceptibility was noted during evaluation.

Foliage:

*Primocane*.—Leaves: large; mature compound leaf average width 17.53 cm; average length 11.73 cm. Leaflet: Average width 8.44 cm; average length 9.91 cm; shape ovate with acute to acuminate apex and obtuse to subcordate base; margin serrate, serration teeth average length 0.24 cm and average width 0.42 cm; moderate pubescence on abaxial side and sparse on adaxial side, covering entire surface; number of leaflets per compound leaf is 3 to 5. Color: Base abaxial Green Group (138B); adaxial Green Group (137A); midpoint abaxial Green Group (138B); adaxial Green Group (137A); terminal abaxial Green Group (138B); adaxial Green Group (137A). Petioles: Length: average 1.45 cm; color: Yellow-Green Group (144B); texture is lightly pubescent. Petiolules: Length: average 0.95 cm; color: Yellow-Green Group (144B); texture smooth. Stipules: Length: average 11.4 mm; width: average 1.82 mm; texture smooth.

*Floricane*.—Leaves: Medium; mature compound leaf average width 10.76 cm; average length 9.74 cm. Leaflet: Average width 5.4 cm; average length 6.92 cm; shape ovate with acute to acuminate apex and obtuse to subcordate base; margin serrate, with serration teeth average length 0.26 cm and average width at base 0.28 cm; moderate pubescence on abaxial side and sparse on adaxial side, covering entire surface. Average number of leaflets per compound leaf is 3 to 5. Color: base abaxial Green Group (138B); adaxial Green Group (137A); midpoint abaxial Green Group (138B); adaxial Green Group (137A); terminal abaxial Green Group (138B); adaxial Green Group (137A). Petioles: Average length 2.6 cm; color: Yellow-Green Group (144B); texture is lightly pubescent. Petiolules: Average length 0.76 cm; color: Yellow-Green Group (144B); texture lightly pubescent. Stipules: Average length 7.64 mm; average width: 1.52 mm; texture is lightly pubescent.

Flowers:

*Floricane*.—Date of bloom: First bloom 1 May, full bloom 7 May, last bloom approximately 25 May. Petal color: White group 155B. Reproductive organs: Stamens — semi-erect, numerous. Pistils — numerous. Pollen — normal, fertile, and abundant. Flower diameter: average 3.87 cm. Petal size: Average length: 1.89 cm; average width: 1.47 cm. Average number flowers per cluster: 2-3. Average number of petals per flower: 5. Number of sepals per flower: 5. Peduncle length: average 45.5 mm. Peduncle color: Green group (143-C). Cyme type: Elongate simple dichasial cyme.

*Primocanes*.—Date of bloom: First bloom 12 July, full bloom 26 July, last bloom approximately October 1$^{st}$ depending on frosts and fall temperatures. Petal color: White Group (155C). Reproductive organs: Stamens — numerous. Pistils — numerous. Pollen — fertile and abundant unless temperatures exceed 85 to 90° F., where pollen production can be reduced. Flower diameter: average 4.38 cm. Petal size: Average length: 2.1 cm; average width: 1.43 cm. Average number flowers per cluster: Average 10.4. Average number of petals per flower: Average 5.6. Number of sepals per flower: Average 5.2. Peduncle length: Average 27.66 mm. Peduncle width: Average 4.79 mm. Peduncle color: Yellow-Green Group (146D). Cyme type: Elongate simple dichasial cyme.

Fruit:

*Floricane*.—Maturity: 12 June. Size: Medium, primary fruit average 7.14 g, secondary fruit average 5.8 g. Diameter of fruit at primary position on inflorescence: equator average 19.0 mm; base pole average 15.5 mm; terminal pole average 14.3 mm. Diameter of fruit at secondary positions on inflorescence: equator average 18.8 mm; base pole average 15.5 mm; terminal pole average 13.1 mm. Length (primary fruit): average 35.4 mm. Shape: Oblong to slightly ovate. Color: Black Group (202A). Soluble solids: 10.4% pH: 3.4. Titratable Acidity: 1.02% expressed as citric acid equivalents. Uses: Dwarf plant for container gardening on patios, and home gardens.

*Primocane*.—Maturity — First ripe fruit date 1 September, can fruit until frost depending on environment and cultural management. Size: Medium to small, primary fruit average 6.4 g, secondary average 6.7 g. Diameter of fruit at primary position on inflorescence: equator average 20.2 mm; base pole average 17.9 mm; terminal pole average 11.0 mm. Diameter of fruit at secondary positions on inflorescence: equator average 20.7 mm; base pole average 17.9 mm; terminal pole average 13.8 mm. Length (primary fruit): Average 27.4 mm. Shape: Oblong to slightly ovate. Color: Black Group (202A). Drupelet size: Average 5.8 mm long by 5.2 mm wide. Uses — Fresh market use for home gardens and container gardening is the primary market.

The cultivar: The most distinctive feature of the cultivar is the dwarf plant habit due to a shortened internode length, which is one half to one third the internode length of a typical erect blackberry cultivar. This feature gives the young primocanes a distinct, columnar appearance due to close spacing of the leaves. Other distinct features are the thornless canes and primocane fruiting habit.

It is claimed:

1. A new and distinct cultivar of blackberry plant named 'APF-236T', substantially as illustrated and described.

* * * * *